United States Patent [19]

Young

[11] 4,308,875
[45] Jan. 5, 1982

[54] AMNIOCENTESIS NEEDLE

[75] Inventor: Ruperto S. Young, Amsterdam, N.Y.

[73] Assignee: Universal Medical Instrument Corporation, Ballston Spa, N.Y.

[21] Appl. No.: 242,713

[22] Filed: Mar. 11, 1981

[51] Int. Cl.$^3$ .............................................. A61B 10/00
[52] U.S. Cl. ................................... 128/753; 128/760; 128/347; 128/361
[58] Field of Search ............... 128/763, 760, 770, 753, 128/754, 765, 766, 347, 348, 361, 214.4

[56] References Cited

U.S. PATENT DOCUMENTS

| | | | |
|---|---|---|---|
| 1,845,727 | 2/1932 | Slaughter | 128/347 X |
| 3,459,188 | 8/1969 | Roberts | 128/347 |
| 3,547,119 | 12/1970 | Hall | 128/214.4 |
| 3,565,074 | 2/1971 | Foti | 128/214.4 |
| 3,680,562 | 8/1972 | Wittes et al. | 128/347 |
| 3,698,396 | 10/1972 | Katerndahl et al. | 128/347 |
| 4,153,058 | 5/1979 | Nehme | 128/347 |
| 4,270,535 | 6/1981 | Bogue et al. | 128/214.4 |
| 4,280,508 | 7/1981 | Barrada | 128/765 X |

Primary Examiner—Dalton L. Truluck
Attorney, Agent, or Firm—Walter F. Wessendorf, Jr.

[57] ABSTRACT

Discloses an amniocentesis needle for use in performing amniocentesis to obtain a amniotic fluid and fetal debris from a pregnant woman's uterus for diagnostic purposes. The amniocentesis needle comprises a hollow needle and a stylet. The hollow needle has a lumen removably and complementally receiving the stylet in close-fitting relationship. The hollow needle has a non-cutting tip and a distal portion which has side holes communicating with the lumen.

6 Claims, 4 Drawing Figures

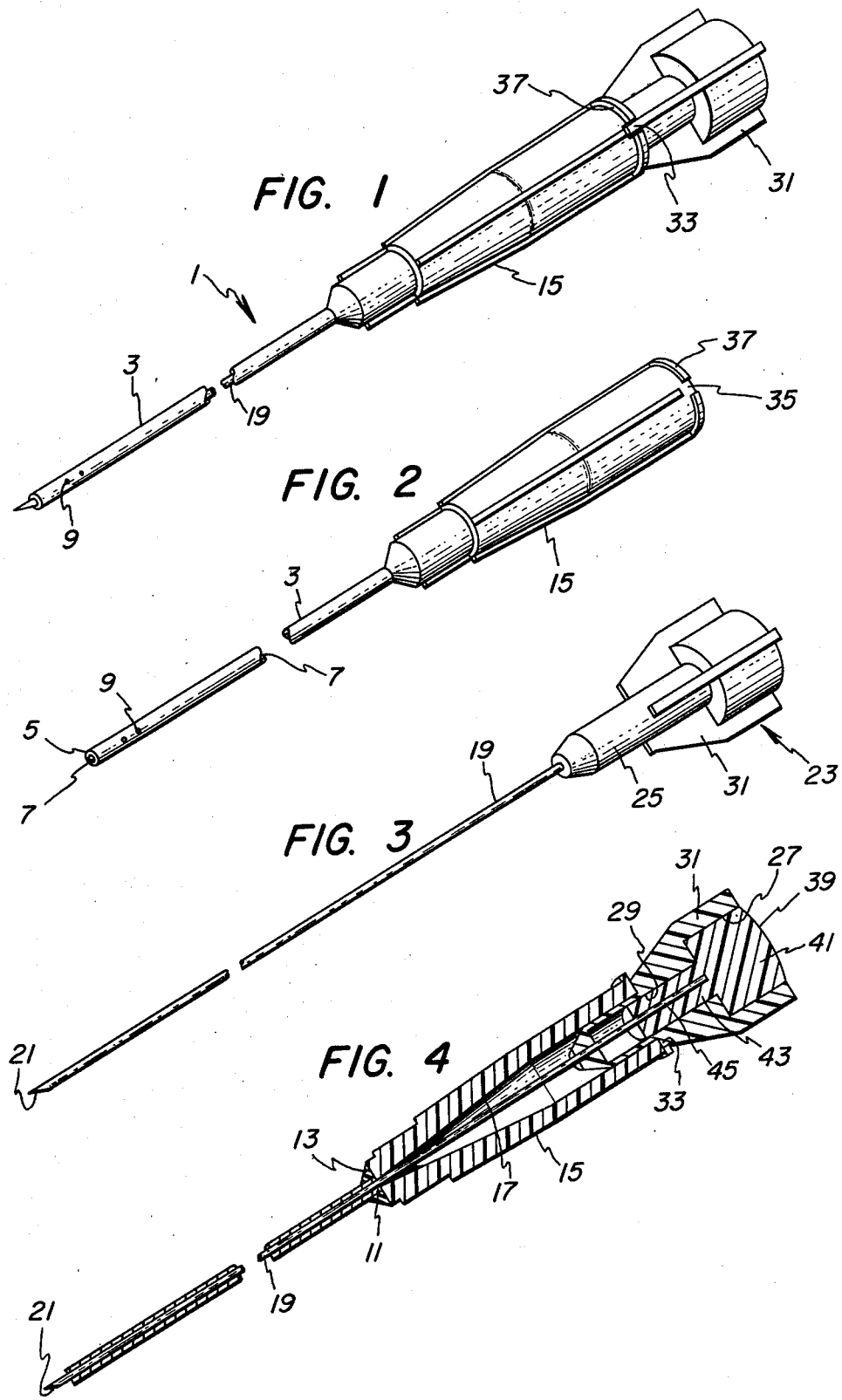

AMNIOCENTESIS NEEDLE

BACKGROUND OF THE INVENTION

1. Technical Field

This invention relates to the procedure of amniocentesis and, in particular, relates to a needle for specific use in such procedure.

Amniocentesis is a procedure utilized to obtain 10 to 20 cc of amniotic fluid from a pregnant woman's uterus for diagnostic purposes. Such fluid is obtained, in the prior art, by inserting a long spinal needle, having a sharp-cutting tip, through the skin, fascia and uterine muscle into the uterine cavity and obtaining therefrom such amniotic fluid by aspiration. Complications, including trauma, hemorrhage and infection have resulted from employing such prior-art surgical needle in such procedure. Concomitantly, the fetus, umbilical cord or placenta may be punctured by such sharp-cutting surgical needle and with such resulting injuries that vary from scratching of parts of the fetus to intrauterine hemorrhage, causing fetal distress and intrauterine death. Fetal pneumothorax and cord hematomas have occurred.

Prior to this invention, there was no safe needle specifically designed for this procedure. The medical literature is replete with documented cases substantiating the prior-art problems, to wit: fetal bleeding and death from puncture of the umbilical cord; free flow of blood from needle puncture of the umbilical cord wrapped around the baby's neck with puncture of the nuchal cord; puncture through a vessel on the fetal surface of the placenta; thoracic puncture resulting in pneumothorax; laceration of the fetal spleen with rupture of the membranes; surgical emphysema and pneumothroax; puncture of the eye requiring its subsequent surgical removal; spontaneous abortion resulting from leakage of amniotic fluid; gangrene of fetal limb as a result of the subclavian artery being punctured; amputations of the fetal limbs within the mother's womb; blindness resulting from ocular puncture; puncture of the fetal peritoneal cavity causing ileal atresia and ileocutaneous fistula; obstruction of the small bowel; scars all over the fetal bodies from needle laceration and needle scratchings; laceration of the spleen, cardiac tamponade, subdural hematoma, arteriovenous fistula; rupture of fetal membranes; the complications of needle-tract endometriosis; respiratory difficulties, major orthopaedic deformities, premature ruptures of the membranes, hemorrhage; needle injury to the myocardium, lung, liver, spleen and brain; fetal exsanguination.

The problems with utilizing such spinal needle with its sharp-cutting tip are the potential and actual injuries to the fetus. This susceptibility for causing injuries arises from the fact that the needle must be manipulated and otherwise moved while in the uterus to obtain the required quantity of amniotic fluid along with some fetal debris for diagnostic purposes. The needle further must be appropriately manipulated and moved in the uterus to free the tip of the spinal needle from any clogging debris.

Accordingly, the object of the invention is to contribute to the solution of the discussed problems of the prior art by providing a safe amniocentesis needle specifically designed and constructed for such diagnostic procedure with the possibility of any injury to the fetus minimized and with any clogging of the needle likewise minimized.

The hollow needle of this invention is specifically designed and constructed to aspirate fluid with a maximum of suction but with a minimum of negative (suction) pressure. The four side holes within 1 cm of the needle tip minimize disturbance of the environment in the amniotic cavity and fetus. The five holes, i.e., the lumen of the hollow needle and four side holes cooperate to equalize suction. The external diameter of the hollow needle is kept to a minimum to minimize unnecessary trauma to the mother, her uterus and tissue. Tissue damage occurs in the prior art due to the larger puncture hole along with the leakage of fluid. Since the four side holes are within 1 cm of the needle tip, the sampling of amniotic fluid is uncontaminated because the effective aspiration area of the hollow needle is minimal. Hence, pure and uncontaminated amniotic fluid can be aspirated. In the prior art, contaminated fluid is drawn from the amniotic cavity when blood from the placenta or afterbirth blood from the mother's blood vessel or tissue is drawn. If such procedure is contaminated, then the procedure must be repeated with the risk of injury and trauma. The hollow needle has a blunt, round and non-cutting tip in order that it can be manipulated and otherwise moved while it is in the womb. Hence, needle injury to the fetus upon penetration or subsequent movement of the needle tip hardly presents a problem because any potential fetal injury is minimal.

SUMMARY OF THE INVENTION

In accordance with the invention, there is provided an amniocentesis needle comprising a hollow needle having a blunt, round, non-cutting tip and multiple communicating side holes at its distal portion. The lumen of such hollow needle removably and complementally receives therein in close-fitting relationship, a solid stylet having a sharp-cutting tip for penetration through the skin, fascia and uterine muscle. After such penetration and introduction of the needle into the amniotic cavity of the uterus, the stylet is removed entirely from such hollow needle. Accordingly, since such needle has a blunt, round and non-cutting tip, it can be manipulated and otherwise moved while in the uterus with any potential injury to the fetus kept to a minimum. The multiple side holes at the distal portion of such hollow needle provide for easy aspiration and removal, for diagnostic purposes, of not only amniotic fluid, but also removal of fetal debris without clogging.

BRIEF DESCRIPTION OF THE DRAWINGS

The object of the invention and other objects of the invention should be discerned and appreciated by reference to the drawings wherein like reference numerals refer to similar parts throughout the several views, in which:

FIG. 1 is a view of the assembled hollow needle and stylet;

FIG. 2 is a view of the hollow needle;

FIG. 3 is a view of the stylet;

and FIG. 4 is a sectional view of the assembled hollow needle and stylet.

DESCRIPTION OF THE PREFERRED EMBODIMENT

In FIG. 1 of the drawings, reference numeral 1 generally refers to the invention of the amniocentesis needle comprising a hollow needle 3 having a blunt, round, non-cutting tip 5 at its distal end, a lumen 7 and four side holes 9 at the distal portion of needle 3 communicating with lumen 7, and with the two side holes 9 stacked on one side being symmetrical with the two side holes 9 stacked on the other side, or otherwise described as two longitudinally aligned side holes 9 on one side of hollow needle 3 being in symmetrical arrangement radially with two longitudinally aligned side holes 9 on the other side of hollow needle 3. The diameter of each of the side holes 9 is slightly less than the diameter of lumen 7. The side holes 9 are within 1 cm of the tip 5 of hollow needle 3. Such side holes 9 are disposed, arranged and constructed, as described, to be consistent with the material strength of the stainless-steel hollow needle without weakening same. The hollow needle 3 is designed with the optimal internal and external diameters suited for the procedure in that the internal diameter is the minimum lumen 7 necessary for the satisfactory passage of amniotic fluid and fetal debris while the external diameter of the hollow needle 3 is reduced to the smallest size feasible to reduce maternal tissue damage and also reduce the leakage of amniotic fluid through the needle tract. The internal diameter of the lumen 7 is 0.66 mm while the external diameter of the hollow needle can range from 0.91 to 0.96 mm.

With reference to the maternal complications from the larger needle tract of the prior art, the medical literature reports endometriosis of the uterine wall, along the needle tract, following amniocentesis. The small needle tract of this invention obviates this complication. Endometriosis is a condition where the tissue lining of the uterus is implanted in the uterine wall and behaves like a tumor.

Since the side holes 9 are confined to the distal 1 cm of the needle tip 5, the sample from the amniotic fluid will be free of contamination. And inasmuch as determination of the chemistry and enzyme level of the amniotic fluid is microscopic, any contamination with material from maternal blood vessels or the placenta will nullify the study, necessitating repitition of the procedure.

Moreover, in pre-caesarean section studies to determine fetal lung maturity, a contaminated specimen will give abnormally high enzyme reading and, therefore, a false reading that the baby is ready for delivery. If so delivered, the baby may die from suffocation due to immature lungs unable to absorb atmospheric oxygen.

The uppermost or proximal portion 11 of hollow needle 3 is suitably fixed to the lowermost or distal portion 13 of female adapter 15. Female adapter or needle hub 15 is of open-cylindrical configuration and has an interior portion 17 tapered divergingly from lowermost portion 13.

The lumen 7 of hollow needle 3 removably and complementally receives therein in close-fitting relationship, solid stylet 19 of stainless-steel material, having a beveled, sharp-cutting tip 21. When properly assembled, the distal cutting tip 21 of stylet 19 extends slightly beyond the blunt, round, non-cutting tip 5 of hollow needle 3; however, such distal cutting tip 21 should not project more than 1 millimeter beyond such blunt, non-cutting tip 5.

The stylet head or hub 23 has a male body portion 25, a cylindrical cavity 27 and reduced shoulder portion of a cylindrical cavity 29 having four symmetrically disposed and raised webs 31 to present externally thereby a somewhat square configuration to facilitate manipulation thereof. One of the raised webs 31 has a projecting nub 33 which is received by a recess 35 in flange 37 of female adapter 15 to thereby prevent relative rotation therebetween.

Such cylindrical cavity 27 and reduced shoulder portion of cylindrical cavity 29 complementally receive in suitably fixed relationship an integral plug 39 having a cylindrical portion 41 and reduced cylindrical portion 43, respectively.

The upper end or proximal portion 45 of solid stylet 19 is concentric with and is fixedly carried by the male body portion 25, and reduced cylindrical portion 43 of plug 39.

In using the amniocentesis needle 1 of this invention, the physician can obtain the amniotic fluid by either transabdominal or suprapubic amniocentesis. The physician utilizes sonography to locate and thereby enable himself to visualize the fetus, placenta and an adequate pocket of fluid, and to determine the location and depth to which the needle will be inserted. Women are of different weight, height and build. Accordingly, from the outer skin through the fascia and uterine muscle to the amniotic cavity varies from 2 to 3 inches; and the fluid in the amniotic cavity likewise varies from 250 cc to 1,500 cc.

With hollow needle 3 and stylet 19 assembled, and with nub 33 in recess 35, the physician appropriately manipulates the exterior of female adapter 15 and the raised webs 31 of stylet head 23, and inserts, at such determined location, such assembled needle through the skin, fascia and uterine muscle and into the amniotic cavity of the uterus of the depth ascertained to be sufficient by such prior diagnostic sonography in order that amniotic fluid may be aspirated therefrom along with fetal debris. Thereupon, stylet 19 is removed from hollow needle 3, the male distal portion of a syringe is appropriately disposed in female adapter 15 and amniotic fluid and fetal debris are aspirated through lumen 7 and side holes 9 which communicate with lumen 7.

Sometimes hollow needle 3 must be moved by adjusting same up or down in order that amniotic fluid can be located for aspiration. Upon moving hollow needle 3 in the amniotic cavity, the part of the hollow needle 3 that can both make contact with the fetus, placenta or umbilical cord and cause injury from such contact is tip 5. However, since tip 5 is blunt, round and non-cutting, the likelihood of any injury from such contact by tip 5 is remote and minimal.

It should further be appreciated that lumen 7 along with communicating side holes 9 contribute to and make possible the uninterrupted aspiration of amniotic fluid along with such fetal debris that can be aspirated.

Having thusly described my invention, I claim:

1. An amniocentesis needle for use in performing amniocentesis, to obtain amniotic fluid and fetal debris from a pregnant woman's uterus for diagnostic purposes; said amniocentesis needle comprising a needle hub, hollow needle, stylet hub and stylet, said hollow needle having a distal end and a proximal portion, said needle hub receiving and carrying said hollow needle at said hollow needle's said proximal portion, said stylet hub having a proximal portion, said stylet hub receiving and carrying said stylet at said stylet's said proximal portion, said hollow needle having a lumen, said needle hub being of open cylindrical configuration, and, in assembled relationship for use preparatory to performing amniocentesis: said lumen removably and complementally receiving said stylet therein in close fitting relationship and said needle hub receiving said stylet hub in mounting relationship with said stylet hub facilitating manipulation thereof in performing amniocentesis, said stylet having a sharp-cutting tip at its distal end to penetrate the skin, fascia and uterine muscle of the pregnant woman to allow said hollow needle, after removal of said stylet from said hollow needle, to be disposed into the amniotic cavity for aspiration therefrom of amniotic fluid and fetal debris; said amniocentesis needle having means on its said distal end cooperating to permit said hollow needle to be manipulated and otherwise moved while in the uterus without injury to the fetus; said amniocentesis needle being of such size to obviate trauma to the pregnant woman, her uterus and tissue, the leakage of amniotic fluid through the needle tract, and to obviate endometriosis; said amniocentesis needle having means, axially spaced from its said distal end, cooperating to minimize suction pressure in the uterine cavity and thereby to obviate disturbance of the fetal environment, to equalize suction of amniotic fluid, to aspirate pure and uncontaminated amniotic fluid and fetal debris without clogging.

2. An amniocentesis needle in accordance with claim 1, wherein said hollow needle has a blunt, round and non-cutting tip constituting said means cooperating to permit said hollow needle to be manipulated and otherwise moved while in the uterus without injury to the fetus.

3. An amniocentesis needle in accordance with claim 1, wherein said hollow needle has side holes constituting said means cooperating to minimize suction pressure in the uterine cavity and thereby to obviate disturbance of the fetal environment.

4. An amniocentesis needle in accordance with claim 3, wherein said side holes comprise two longitudinally aligned side holes on one side of said hollow needle that are in symmetrical arrangement radially with two longitudinally aligned side holes on the other side of said hollow needle.

5. An amniocentesis needle in accordance with claim 4, wherein the diameter of each of said side holes is slightly less than the diameter of said lumen, wherein said hollow needle has a tip and wherein said side holes are within 1 cm of said hollow needle's tip.

6. An amniocentesis needle in accordance with claim 3, wherein said side holes and said lumen cooperate to equalize suction of amniotic fluid, to aspirate pure and uncontaminated amniotic fluid and fetal debris without clogging.

* * * * *